United States Patent
Legastelois et al.

(10) Patent No.: US 9,329,181 B2
(45) Date of Patent: May 3, 2016

(54) MAGNETIC IMMUNOCHROMATOGRAPHIC TEST METHOD AND DEVICE

(75) Inventors: Stephane Legastelois, Saint Andeol le Chateau (FR); Petr Ivanovich Nikitin, Moscow (RU); Jean-Marie Billiotte, London (GB)

(73) Assignee: MAGNISENSE TECHNOLOGY LIMITED (CY)

( * ) Notice: Subject to any disclaimer, the term of this patent is extended or adjusted under 35 U.S.C. 154(b) by 1466 days.

(21) Appl. No.: 12/293,726

(22) PCT Filed: Mar. 21, 2007

(86) PCT No.: PCT/IB2007/000700
§ 371 (c)(1),
(2), (4) Date: Dec. 15, 2010

(87) PCT Pub. No.: WO2007/107858
PCT Pub. Date: Sep. 27, 2007

(65) Prior Publication Data
US 2011/0117672 A1  May 19, 2011

Related U.S. Application Data

(60) Provisional application No. 60/783,856, filed on Mar. 21, 2006.

(51) Int. Cl.
*G01N 33/558* (2006.01)
*G01N 33/58* (2006.01)

(52) U.S. Cl.
CPC ............ *G01N 33/558* (2013.01); *G01N 33/585* (2013.01); *G01N 2446/00* (2013.01)

(58) Field of Classification Search
USPC .......................................................... 436/514
See application file for complete search history.

(56) References Cited

U.S. PATENT DOCUMENTS

5,157,332 A  10/1992  Reese
5,223,220 A  6/1993  Fan et al.
(Continued)

FOREIGN PATENT DOCUMENTS

EP  1641565 A1  4/2006
WO  WO 00/79276  12/2000

OTHER PUBLICATIONS

Lany M et al: Superparamagnetic microbead inductive detector, Review of Scientific Instruments, American Institute of Pysiscs, US, vol. 76, No. 8, Jul. 20, 2005.

*Primary Examiner* — Melanie Y Brown
*Assistant Examiner* — Rebecca Martinez
(74) *Attorney, Agent, or Firm* — Cantor Colburn LLP (57) ABSTRACT

Method for detecting and quantifying an analyte in a liquid sample, using a test strip and magnetic particles as a detectable label and based on the detection of an amount of magnetic particles which become bound to a reading zone of a test strip as a result of performing the method, said amount being linked through a function to the analyte content of the sample, wherein the magnetic particles exhibit a nonlinear magnetization characteristic, which test strip is made of porous material and is arranged inside a case, cartridge or the like to form an assay device, wherein in its part surrounding the reading zone, the case is made of a material that is permeable to magnetic field, wherein for the reading of the reaction, the assay device is positioned in a measure cell of a magnetic reading device which detects the amount of magnetic particles in the reading zone by submitting it to at least one excitation magnetic field having about 90% of its power within one frequency band or a plurality of frequency bands, and the reading device measures the induced magnetic response field outside said frequency band or said plurality of frequency bands.

21 Claims, 5 Drawing Sheets

(56) References Cited

U.S. PATENT DOCUMENTS

| | | | |
|---|---|---|---|
| 6,046,057 A | 4/2000 | Nazareth et al. | |
| 6,518,747 B2 | 2/2003 | Sager et al. | |
| 6,541,277 B1 | 4/2003 | Kang | |
| 6,713,271 B1 * | 3/2004 | Feistel | 435/7.92 |
| 7,323,139 B2 | 1/2008 | LaBorde et al. | |
| 2003/0027197 A1 | 2/2003 | Nikitin et al. | |
| 2003/0044317 A1 * | 3/2003 | Catt et al. | 422/58 |
| 2004/0053423 A1 * | 3/2004 | LaBorde | 436/514 |
| 2004/0171172 A1 * | 9/2004 | Laitinen et al. | 436/514 |
| 2005/0221386 A1 * | 10/2005 | Turner et al. | 435/7.1 |
| 2006/0257956 A1 | 11/2006 | Basset et al. | |
| 2007/0155024 A1 | 7/2007 | Miethe et al. | |
| 2008/0020482 A1 | 1/2008 | Raj | |

* cited by examiner

MAGNETIC IMMUNOCHROMATOGRAPHIC TEST METHOD AND DEVICE

CROSS REFERENCE TO RELATED APPLICATIONS

This application claims benefit of U.S. Provisional Application No. 60/783,856, filed Mar. 21, 2006 (which is hereby incorporated by reference).

The present invention is related to a method for the detection and quantification of an analyte, in a sample. The invention is also related to a lateral-flow test device.

EP 1 262 766 describes detecting and quantifying an analyte in a sample wherein use is made of magnetic particles as detection means. This document discloses particularly the use of micro-columns filled with a porous material defining a reading zone wherein a ligand is immobilized. This ligand is chosen so as to specifically retain the analyte to be detected. The sample is first mixed with magnetic particles bound to a reagent that is able to react with the analyte leading to the formation of a complex comprising the analyte, the reagent and the magnetic particle. This mixture is then placed in the micro-column and is allowed to diffuse therein, and the complex is retained by the immobilized ligands. The emission of an appropriate magnetic field allows one to determine the concentration of magnetic particles and finally the concentration of the analyte in the sample. The micro-columns may be emptied with a capillary or porous structure similar to a chromatography column, e.g. micro-granules. The document also provides for the use of a strip of porous material.

U.S. Pat. No. 6,518,747 is also related to using magnetic events to detect a reaction on a planar support plate. This document teaches measuring the accumulation of magnetic particles in a reading zone determined at the surface of the support plate. The detection uses Hall sensors and necessitates a very precise and close positioning of the reading zone on the plate with respect to the magnetic field and thus the precision of the lecture is obtained owing the use of a very thin space inside which the support plate is to be inserted. Thus the precision of the reading is closely related to a very precise positioning of the plate with respect to the reader.

In addition, the naked strips or plates according to EP-A-1 262 766 and U.S. Pat. No. 6,518,747 are difficult to handle before and after the sample has been applied thereon, and are susceptible to contaminations.

Surprisingly, the applicant has found that it is possible to use porous material strips protected by their insertion in a case or the like wherein the label comprises magnetic particles. More surprisingly, the applicant has found that this is economically and practically feasible. Despite the presence of a case surrounding the strip, it is possible to properly submit the magnetic particles to a magnetic field, to detect with great sensitivity the magnetic particles in a reaction or reading zone and to precisely quantify the analyte that is present in the sample. It was not predictable from EP 1 262 766 and U.S. Pat. No. 6,518,747 that the use of a case surrounding the strip would be compatible with the positioning of the magnetic reader and the reading of the reading zone in such a manner that a precise quantification is possible. Thus the device and method of the invention allow the presence of a case or the like while being substantially not sensible to some position variations, including angular variations, of the strip with respect to the magnetic field, without the necessity of placing the strip at a predetermined and very close or equidistant location with respect to the magnetic field generators.

Herein, the words "comprise/comprising" are synonymous with (means the same thing as) "include/including," "contain/containing", are inclusive or open-ended and do not exclude additional, unrecited elements.

SUMMARY OF THE INVENTION

A first object of the present invention is a method for detecting and quantifying an analyte, preferably a biological or chemical compound, in a liquid sample, using a test strip and magnetic particles as a detectable label and based on the detection of an amount of magnetic particles which become bound to a reading zone of a test strip as a result of performing the method, said amount being linked through a function to the analyte content of the sample, wherein the magnetic particles exhibit a nonlinear magnetization characteristic, which test strip is made of porous material and is arranged inside a case, cartridge or the like to form an assay device, wherein in its part surrounding the reading zone, the case is made of a material that is permeable to magnetic field, wherein for the reading of the reaction, the assay device is positioned in a measure cell of a magnetic reading device which detects the amount of magnetic particles in the reading zone by submitting it to at least one excitation magnetic field having about 90% of its power within one frequency band or a plurality of frequency bands, and the reading device measures the induced magnetic response field outside said frequency band or said plurality of frequency bands.

Another object of the invention is a method for detecting and quantifying an analyte, preferably a biological or chemical compound, in a liquid sample, based on the detection of a specific binding event between the analyte linked to magnetic particles (typically to a conjugate) or a conjugate and a ligand immobilized in a reading zone of a test strip, wherein the magnetic particles exhibit a nonlinear magnetization characteristic, which test strip is made of porous material and is arranged inside a case or the like to form an assay device, wherein in its part surrounding the reading zone, the case is made of a material that is permeable to magnetic field, wherein after completion of the reaction between ligand and analyte, the assay device is positioned in a measure cell of a magnetic reading device which detects the amount of magnetic particles in the reading zone by submitting it to at least one excitation magnetic field having about 90% of its power spectral density within one frequency band or a plurality of frequency bands, and the reading device measures the induced magnetic response field outside said frequency band or said plurality of frequency bands.

Another object of the present invention is an assay device for detecting and quantifying an analyte in a liquid sample, which may be used in the method according to the invention. This device comprises a test strip having a sample-receiving zone and a reading zone. In an embodiment, a conjugate pad is present in flow contact with the strip. The test strip is of such a material that allows the liquid sample and the analyte to flow or diffuse from the sample-receiving zone in the direction of and through the reading zone. The test strip is arranged inside a case or the like provided with a sample window facing or in the vicinity of the sample-receiving zone allowing to put the liquid sample into contact with the strip. At least in its part surrounding the reading zone, the case is made of a material that is permeable to a magnetic field. In this part, the case may be made of a blind (non-transparent) material. The case may also be entirely made of a blind (non-transparent) material.

DETAILED DESCRIPTION OF THE INVENTION

Preferably, said function which links the amount of magnetic particles to the analyte content of the sample, is a strictly monotonic function increasing or decreasing in the dosage validity zone. Dosage validity zone is defined as the range of concentrations of the analyte that can be measured with acceptable precision and accuracy.

A material called ligand is immobilized in the reading zone. This ligand is responsible for the binding of the magnetic particles to the reading zone. This binding is dependant from the amount of analyte in the sample. As it will be explained in more details in the following description, the magnetic particles are present in a complex with a reagent to form the so-called conjugate.

The art of strip based or lateral-flow diagnosis comprises different assay principles called sandwich, blocking, blocking-like or inhibition and competition assays. The present invention may be applied to every of them.

Use is made of a movable entity which is labeled, i.e. is bound to one or several magnetic particle(s), directly or indirectly through a binder. The analyte itself may be labeled when it binds to the immobilized ligand, wherein the labeling may occur before putting the sample into contact with the strip or may occur after this contact and during the flow of the sample on the strip. Generally, the entity which is labeled is a reagent bound to one or several magnetic particle(s), directly or indirectly through a binder. This reagent may bind the analyte or compete with him for binding to the immobilized ligand. This labeled reagent will be named conjugate in the following description.

In some embodiments, the test strip has one, several or preferably all of the following features:
  a sample-receiving zone
  a reading zone wherein said ligand is immobilized
  the test strip is of such a porous material that allows the liquid sample and the analyte to flow from the sample-receiving zone in the direction of and through the reading zone
  the test strip is arranged inside a case or the like provided with a sample-introducing window facing or in the vicinity of the sample-receiving zone and allowing to put the liquid sample into contact with the strip
  in its part surrounding the reading zone, the case is made of a material that is permeable to a magnetic field.

The test strip may have in addition one, several or all of the following features:
  a control zone
  a control reagent with a label which is not magnetic label, said control reagent allowing to check whether diffusion of the sample is correct
  the label for the control is a visual label.

In some embodiments, the method has one, several or preferably all of the following features:
  the sample is first put into contact with a conjugate which specifically binds to the analyte when the latter is present in the sample,
  said conjugate is present on and/or in the strip, preferably under a dried form,
  the analyte-conjugate complex so-obtained is allowed to diffuse in the direction of and through the reading-zone where it is immobilized due to binding to the ligand, leading to an immobilized ligand-analyte-conjugate complex.

In other embodiments, the method has one, several or preferably all of the following features:
  the sample and a conjugate able to bind to the analyte as well as to the immobilized ligand are used,
  said conjugate is present on and/or in the strip, preferably under a dried form,
  the analyte in the sample and the conjugate are allowed to bind one to the other
  the immobilized ligand is a homologous (the same analyte or an analogue thereof) of the analyte
  the sample and the conjugate are allowed to diffuse in the direction of and through the reading-zone where only the conjugate not bound to the sample analyte is allowed to bind to the immobilized ligand.

A migration liquid may be used to facilitate the migration of the liquid sample.

In a preferred embodiment, the assay device is positioned with respect to a magnetic reading device in order to submit the reading zone to:
  a step of excitation of the magnetic particles located in the reading zone with an excitation magnetic field having components at frequencies $f_1$ and $f_2$ in its power spectral density, and
  a step of measuring the amplitude of the magnetic field induced by the magnetic particles in response to the excitation at a specific frequency component the $f_i$, the $f_i$ frequency being related to frequency components $f_1$ and $f_2$ by the following relation:
    $f_i = n.f_1 \pm m.f_2$, where m and n are integers $\geq 0$, at least one of m and n being different from 0
the frequency component $f_i$ amplitude being directly proportional to the amount of magnetic particles retained in the reading zone.

In a first embodiment, n is 1 and m is ±2.

In a second embodiment, n or m is zero.

According to a feature, frequencies $f_1$ and $f_2$ may have a value comprised between about 10 Hz and about 10 MHz, in particular from about 10 Hz and about 1 MHz, for example from about 10 Hz and about 100 kHz. For instance, one of the frequencies may be 1 kHz and the other 100 kHz.

According to a feature, the magnetic particles exhibit a nonlinear magnetization characteristic.

The magnetic particles are typically from about 5 nm to about 50 µm in size, preferably from about 10 nm to about 10 µm, more preferably from about 100 nm to about 1 µm. The particles may have a spherical or semi-spherical shape, or any other shape. The particles may be made of the magnetic material itself or of a mixture of this material with a solid or semi-solid matrix. In the latter case, the magnetic material is dispersed in the matrix.

Figure 6:
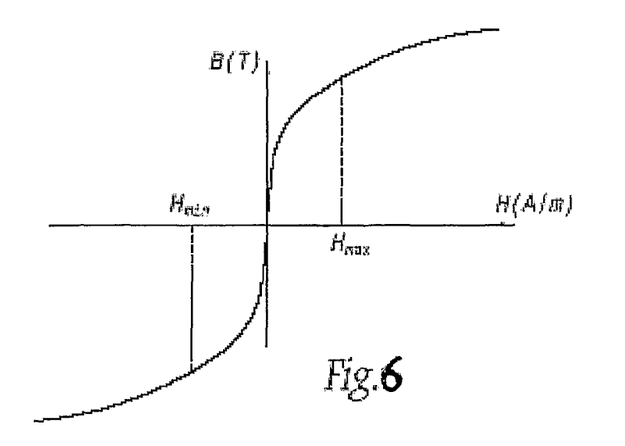
FIG. 6 is a graph representing the characteristic of the magnetic induction) ($\vec{B}$) of a superparamagnetic material depending on the magnetic field ($\vec{H}$) induced in the material.

In a preferred embodiment, the particles are superparamagnetic. In a feature, these particles are made of ferromagnetic elements in a matrix and the maximum width of the ferromagnetic elements is sufficiently small in order that each element taken individually has a magnetic cycle B(H) having the same properties than the one represented on FIG. 6. Typically, the maximum width of the ferromagnetic element is chosen to be below about 100 nm and generally below about 20 nm. This maximum width of the element below which the element becomes superparamagnetic depends on the ferromagnetic material used. The superparamagnetism as well as superparamagnetic elements are presented in E. du Trémolet de Lacheisserie and al. <<Magnétisme>> TOME 1, Presses Universitaire de Grenoble, 1999.

Iron oxides are the preferred superparamagnetic elements. To be more complete, it can be specified that the element may be chosen among iron oxides and mixed oxides of iron and another metal, as a metal chosen among Mn, Ni, Zn, Bi, Cu, Co. $Fe_3O_4$ and $Fe_2O_3$ are preferred embodiments. Other examples include: perovskites with superparamagnetic properties, especially Fe-based perovskites; superparamagnetic nickel oxides, cobalt oxides or mixed oxides of these metals;

as well as superparamagnetic metallic alloys, e.g. of the type FeNi or CoNi, especially $Fe_{20}Ni_{80}$.

In another embodiment, the particles are antiferromagnetic. An antiferromagnetic material is one where the spins of magnetic electrons align in a regular pattern with neighboring spins pointing in antiparallel directions. Such material include metals such as chromium, alloys such as FeMn, oxides such as NiO. Reference may also be made to E. du Trémolet de Lacheisserie and al. supra.

In one embodiment, the particles are the silica particles sold by Merck Chimie under the trade name MagPrep® Silica Particles, which contain iron oxide.

The solid or semi-solid matrix is chosen so as to not interfere with the magnetic properties of the element. In a feature, the matrix is diamagnetic.

Semi-solid matrix includes a matrix that is elastically deformable in a reversible manner, such as an elastomer.

Materials for the matrix include: natural, synthetic and artificial polymers, elastomers and gels, silica; for example plastic material, cellulosic material.

The distribution of the superparamagnetic elements in the matrix is such that the distances between the elements within the matrix are sufficient for the so-formed particles to have the same, or substantially the same, superparamagnetic properties than the element.

For the emission of the excitation magnetic field and the signal processing, reference may be made to EP 1 262 766 or WO-A-2004/077044, to which the person skilled in the art may refer. The whole content of these patent applications is incorporated herein by reference. An embodiment is described in the example.

To carry out the method of the invention, use may be made of a magnetic reading device which comprises a measure cell. The measure cell has means allowing the positioning of the strip reading zone so that this zone is covered by the magnetic excitation field. In a preferred embodiment, the case or the like and the cell do have a complementary form and size so as to allow the positioning. According to a method feature, the reading zone in the strip is placed so as to be entirely or substantially entirely covered by the magnetic field. Preferably, only the magnetic particles bound to the reading zone are submitted to the magnetic excitation field and to the reading process.

The magnetic reader may comprise one or several of the following features:
- a coil mounted in the vicinity of the measure cell and able to generate in this space a magnetic excitation (A/m)– (excitation coil)
- the coil is able to generate a magnetic excitation made of the superposition of two monochromatic signals of frequencies $f_1$ and $f_2$
- frequencies may be between about 10 Hz and about 10 MHz (see above)
- a measuring coil
- the same coil generates the magnetic excitation and effect the measure (excitation/measuring coil)
- the coil or coils forms a so-called reading head
- the measure cell is designed so that the magnetic excitation field is in a plan transversal to the test strip length L
- the excitation/measuring coil is cylindrical and delimitates a cylindrical reading space in which the assay device may be put in place for the measurement
- the reading space and the coil may be separated by an internal piece or material forming said space,
- the excitation/measuring process is independent from the angular orientation of the strip within the measure cell, in particular within the cylindrical reading space (angular orientation means that the strip may be placed at any angular position around its longitudinal axis)
- the diameter of the cylindrical space delimited by the coil is up to about 10 mm, preferably comprised between about 4 mm and about 10 mm
- means are provided to place the test device substantially at the center of the measure cell or the cylindrical space
- a filter and an amplitude demodulator, allowing the measure of the intensity of one or several spectral lines
- Lock-in amplifier (digital and/or analogic) which allows to accurately determine the volume of non linear magnetic material in the volume of reading.

According to advantageous features, the measure cell is formed by the space, preferably cylindrical space delimited by the excitation and measuring coil or internal piece or material, the strip is placed inside the measure cell to effect the measurement of the amount of magnetic particles in the reading zone. The strip is placed so as to extend in parallel with the longitudinal axis of the space, with the reading zone substantially or totally contained within the space. Typically, the distance between the strip surface and the internal face of the coil or internal piece or material along a line perpendicular to the longitudinal axis of the reading zone may be between about 0 and about 5 mm, preferably between about 2 and about 5 mm, e.g. between about 3 and about 4 mm.

The porous material of the strip is chosen so as to allow the different substances involved in the test to diffuse at the surface and possibly in depth in the material from the sample-receiving zone along the strip in the direction of the strip end opposed to said receiving zone. Continuous usual materials such as polyethylene, polystyrene, polyamide, e.g. Nylon®, cellulose or derivatives thereof, especially nitrocellulose, may be used. As usual, this material may be placed on a support, such as a plastic support.

The thickness of the strip may vary in a large range. The thickness may be used to provide for a reading zone having a certain thickness or volume, say forming a reading zone with a determined three-dimensional volume, correlated with the degree of sensitivity that is wished, and notably correlated with the threshold of detection and quantification. It can thus be indicated that an increase of the reading zone volume facilitates the detection and quantification of analytes present in small amount in the sample. A further advantage of the present invention is that it may be unnecessary to concentrate the analyte before analysis and rather direct detection and precise quantification is possible.

In one embodiment, the sample is mixed with the conjugate and then the mixture is put in contact with the strip.

In another embodiment, the conjugate is present on the strip or within the strip, optionally on or in a conjugate pad in flow contact with the strip, where it has been impregnated and dried. The sample is put onto the strip or the pad and drives the migration of the conjugate.

The reaction zone contains an immobilized ligand. This ligand may specifically bind the sample analyte. As an alternative, the immobilized ligand may bind the conjugate but may not bind the analyte or the analyte-conjugate complex. As another alternative, the immobilized ligand may bind the sample analyte and a competition conjugate, e.g. a conjugate which is able to compete with the analyte for binding to the ligand.

The conjugate may bind to the sample analyte and/or to the immobilized ligand. It may be specific binding in the sense that the conjugate is specifically designed to bind only to this target (for example a labeled antibody specific to an antigen or another antibody, or a labeled antigen specific to an antibody). The binding to said sample target may also be of a non-specific nature in the sense that the conjugate is able to bind different materials of the same type (for example a labeled immunoglobulin which is designed to bind to human antibodies).

In an embodiment, the conjugate is homologous to said sample analyte, i.e. it may be the same or an analogue thereof, and it competes with the sample analyte for the binding to the immobilized ligand.

In another embodiment, the immobilized ligand is homologous to said sample analyte, i.e. it may be the same or an analogue thereof, and the conjugate may bind to the sample analyte and to the immobilized ligand as well when the conjugate is not bound to the analyte.

In one embodiment, a sandwich type assay is conducted.

In another embodiment, a blocking, blocking-like or competition-type assay is conducted.

According to a feature, the sample is diluted with an acceptable buffer or solvent before contacting with the strip.

Other features concerning the strip material, its structure, its dimensions especially its thickness and the thickness/length ratio will be disclosed in the following description of an assay device according to the invention.

The assay device comprises a test strip having a sample-receiving zone and a reading zone. In an embodiment, a conjugate pad is present in flow contact with the strip. The test strip is of such a material that allows the liquid sample and the analyte to flow or diffuse from the sample-receiving zone in the direction of and through the reading zone. The test strip is arranged inside a case or the like provided with a sample window facing or in the vicinity of the sample-receiving zone allowing to put the liquid sample into contact with the strip. At least in its part surrounding the reading zone, the case is made of a material that is permeable to a magnetic field. The test strip may have a thickness (t) in the range of about 10 µm to about 10 mm. In an embodiment, the strip thickness is between about 0.1 mm and about 0.5 mm, typically between about 0.1 and about 0.3 mm. In another embodiment of thick strip, the thickness is above 0.5 mm and less or equal to about 2 mm.

Typically, the strip width (W) may be between about 1 and about 20 mm, preferably between about 2 and about 10 mm, typically between about 3 and about 7 mm.

In a feature, the reading zone width ($Z_R$) is between about 0.5 and about 5 mm, preferably between about 2 and about 5 mm. This width ideally matches the size of the reading head or of its reading area.

In one embodiment, the case part surrounding the reading zone is made of a blind (non-transparent) material, i.e. it is not possible to see the reading zone with the eye. According to a feature, the case is entirely made of such a blind material. According to a particular modality, the case has a window for visual reading of a control zone.

To have the right thickness (t), the strip can be made in different ways. It can be made of a plurality of superimposed layers (plies). It can be obtained by folding a sheet made of the strip material. It can be a rolled sheet, say made of a sheet rolled on itself with or without superimposed parts. It can also be directly made of a thick continuous material having the selected thickness.

According to a feature, a compound intended to be present on the strip is impregnated and then dried or immobilized in the corresponding area before folding in case of folded sheet or before superimposing the layers in case of a strip made of a plurality of superimposed layers or before rolling to obtain a rolled strip. This way of preparing the strip facilitates the distribution of the compound in depth in the whole zone. This compound may be for instance the ligand to be immobilized in the reading zone or any mobile conjugate or any other movable adsorbed compound.

In an embodiment, the test strip has a zone, possibly a three-dimensional zone, containing a movable conjugate that is a ligand binding to, e.g. specific for the analyte and that comprises a magnetic particle. This zone may be the same or different than the sample-receiving zone.

In another embodiment, a pad is placed in flow contact on a surface of the strip and this pad contains or bears on its surface the movable conjugate. This conjugate pad may be located between the sample-receiving zone and the reading zone or may have the role of sample-receiving zone.

In another embodiment, the test strip or a sample-receiving pad in flow contact with the strip has a three-dimensional zone containing a movable conjugate which is the analyte or an analogue thereof.

In an embodiment, an end of the strip extends outside or near an opened end of the case. This end forms the sample-receiving zone which can be put in contact with the sample.

In a preferred embodiment, the test strip has a (possibly three-dimensional) reading zone containing an immobilized ligand which is specific for the analyte or an analogue thereof, said three-dimensional zone having the thickness (t) of the strip and having a width ($Z_R$) as recited above.

According to a feature, an absorbent pad is placed in contact with the strip at its end opposite to the sample-receiving zone, in order to facilitate the flow of sample.

According to another feature, use is made of a kit comprising said assay device and a syringe or similar device intended to mix the sample and the conjugate. The mixture may then be expulsed on the strip or in the strip from an end thereof.

Advantageously, the test strip has a waste zone for material which did not bound in the reading zone, this waste zone being arranged on the side of the strip opposed to the sample-receiving zone with the reading zone between them. The waste zone may be constituted by the above mentioned absorbent pad.

In another embodiment, the waste zone is simply sufficiently far away from the reading zone not to interfere with the reading. Typically, the distance between the center of the reading zone and the waste zone is equal or above 5 mm, preferably of the order of the size of a reading head of the magnetic reading device.

In still another embodiment, the device is provided with a screen, e.g. a metallic screen, at the level of the waste zone which isolates the waste zone with respect to the magnetic field and avoids or limits magnetic interferences due to the magnetic particles which are present in the waste zone. This screen may be made of a sheet of material in direct contact or not in direct contact with the strip; it may be for example attached to the strip or to the case, in front in direct contact of the waste zone. It may be also a material that has been sprayed or similar onto the waste zone of the strip or a surface of the casing in front of the waste zone. The metallic material is preferably Cu or Al or any metal having similar or superior conductivity than Cu or Al.

In still another embodiment, the waste zone and possibly the corresponding part of the case is removable.

The method and device of the invention may be used for detecting and quantifying biological components in a body fluid sample, e.g. blood, plasma, urine. It may be used to detect and quantify the presence of an antigen (e.g. bacteria, virus, parasite, proteins and fragments thereof), an antibody or any other biological compound such as haptens, proteins, gene probes, natural or synthetic oligo- or polynucleotides, natural or synthetic mono-, oligo- or polysaccharides, lectins, avidin, streptavidin, biotin, growth factors, hormones, receptor molecules, allergens.

In case of antibody-antigen reaction, the conjugate may be either an antigen or an antibody, for instance an antigen that recognizes specifically an antibody to be detected in the sample or an antibody that specifically recognizes an antigen to be detected in the sample.

The immobilized ligand may be an antibody specifically recognizing the antigen that is to be detected in the sample and that is present in the antigen-conjugate complex or it may be an antigen that specifically recognizes an antibody to be detected in the sample and that is present in the antibody-conjugate complex.

The method and device of the invention thus allows one to carry out any type of sandwich or competition assay. The invention allows one to establish a direct relationship between the sample concentration for the analyte and the magnetic reading done, this giving access to detection and quantification of the analyte.

As it is well known, the antibodies may be polyclonal or monoclonal, or may be fragments of antibodies, and the antigens may be natural or prepared through chemical synthesis or genetic engineering. The person skilled in the art has access to antibodies and antigens that may be used to detect and quantify a given analyte in a given sample.

The method and device of the invention may also be used for detecting and quantifying chemical entities or compounds, such as antibiotics, drugs of abuse, chemical contaminants, allergens.

The present invention will now be described in further details by way of non-limiting examples and by reference to the attached drawings wherein.

Figure 1:
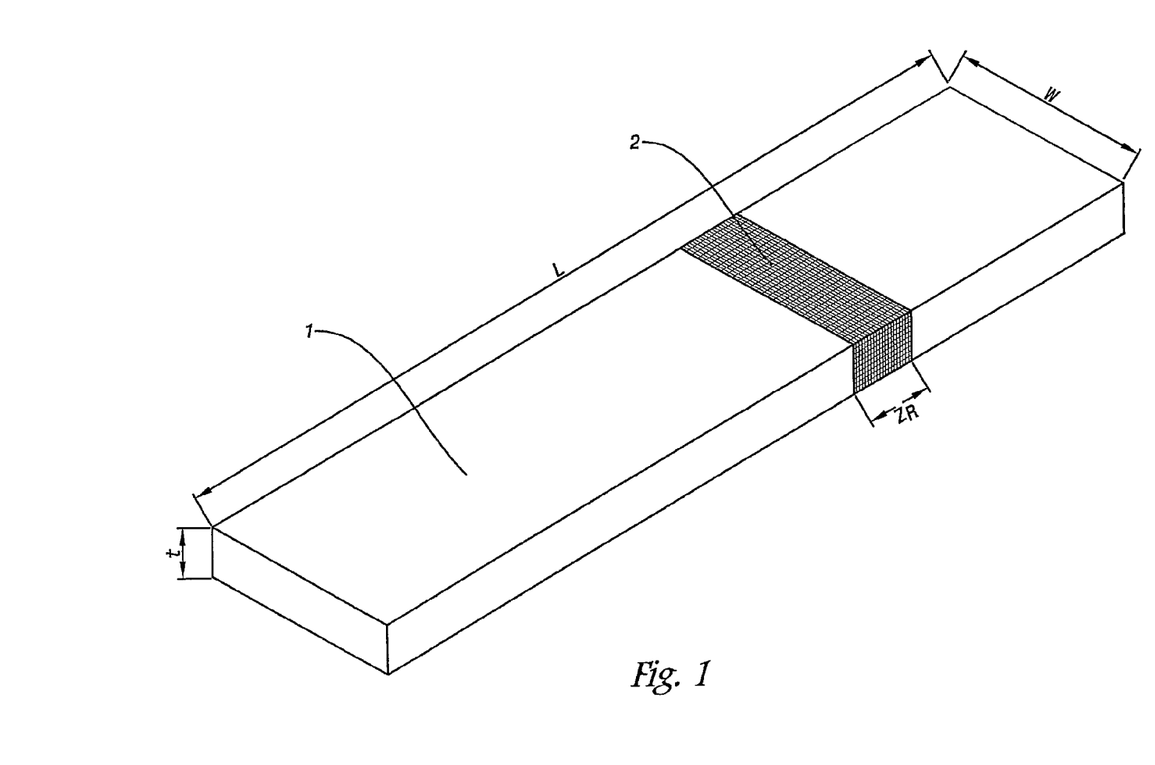
FIG. 1 is a schematic representation of a strip 1 explaining the following dimensional definitions: strip length L, strip width W, strip thickness t and reading zone 2 width $Z_R$.
Figure 2:
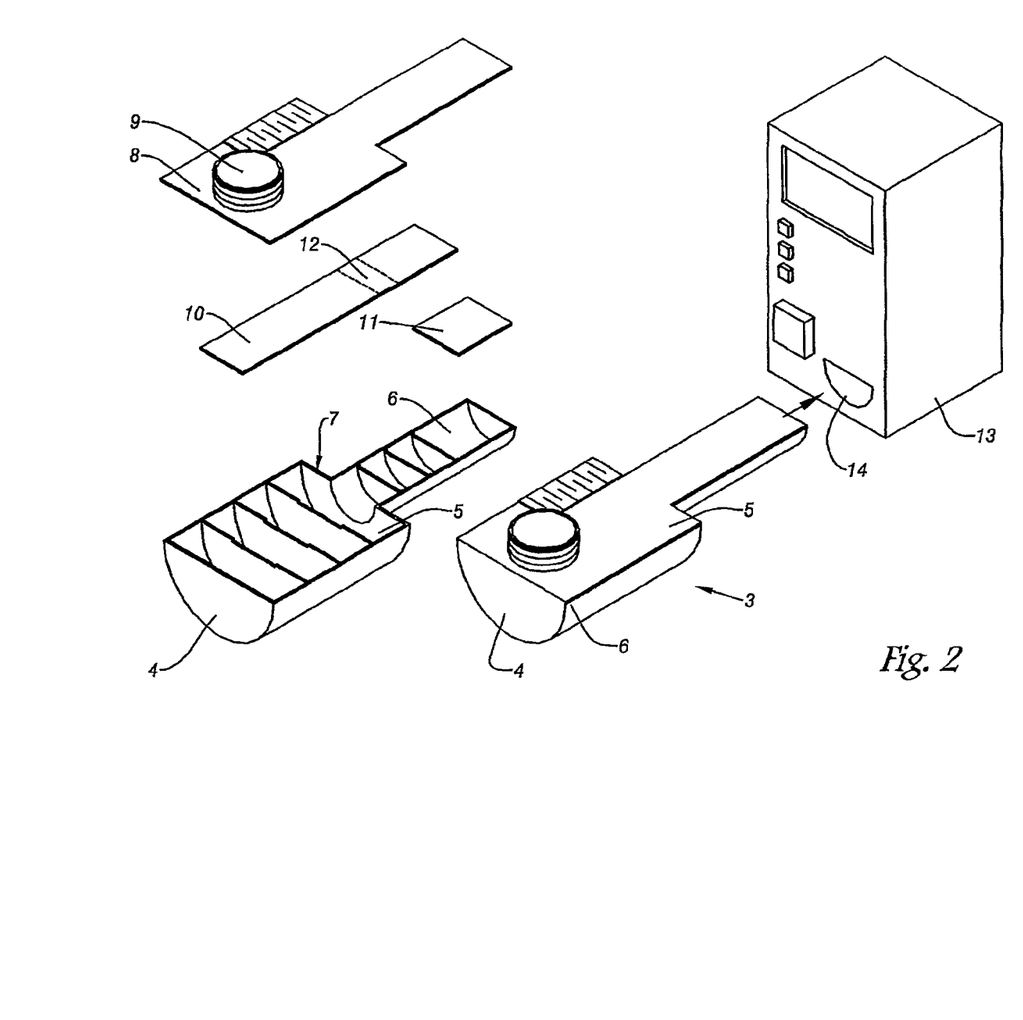
FIG. 2 is a schematic representation of a first test device embodiment construction and use.

FIG. 2 depicts in exploded form the various components of an assay device according to a first embodiment, the assay device once assembled and its cooperation with a magnetic reading device. The assay device 3 is made of a staged case 4 of semi-circular section and having a part 5 and a part 6 wherein part 6 is of smaller section with a shoulder 7; a cover 8 having an aperture 9 and having a shape complementary to that of the case; a strip 10 and an absorbent pad 11. A reaction zone 12 has been represented using dashed lines. Numeral reference 13 designates a magnetic reader having a semi-circular opening 14 in which part 6 of the case may be introduced until abutment of shoulder 7.

Figure 3:
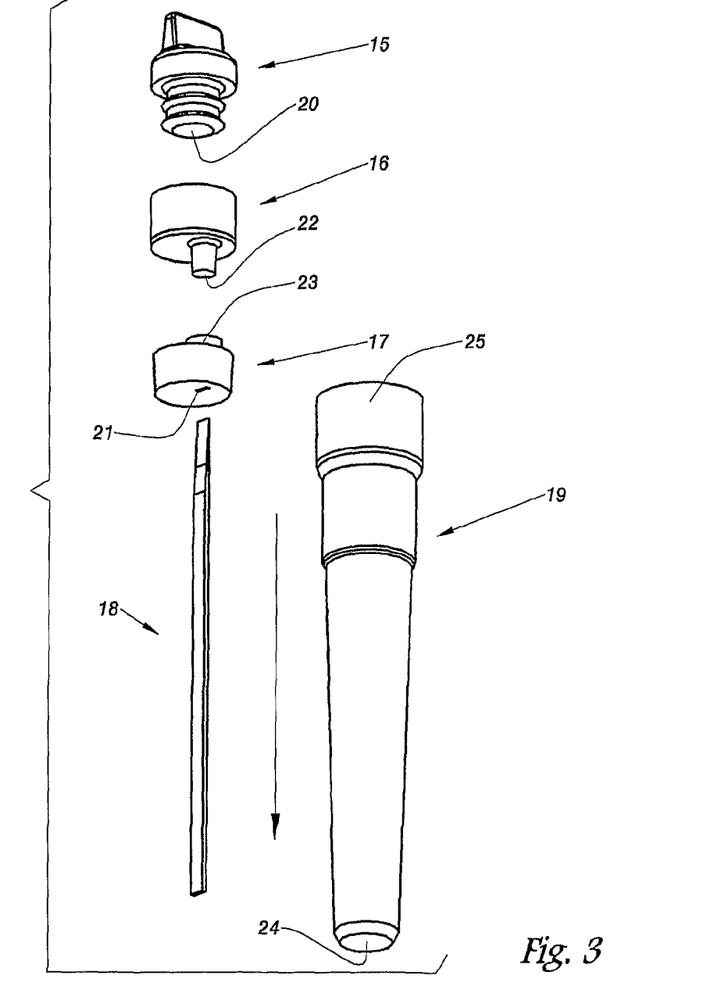
FIG. 3 is an exploded representation of a second test device embodiment.

FIG. 3 depicts in exploded form a test device comprising a buffer container 15, a sample collector 16, a filter 17, a test strip 18 and a test strip case 19.

Container 15 has a pierceable membrane 20, is hollow and contains a buffer fluid. Sample collector 16 may be connected to the container 15 through screwable complementary portions. By screwing both portions beyond a given position, membrane 20 is pierced by means (not represented) present in collector 16. This allows the buffer liquid to dilute the sample in the collector 16.

Filter 17 comprises an aperture 21 that serves securing the test strip and a filter material (not shown) that filters sample impurities, absorbs and contains buffer solution and sample, and provides a controlled fluid flow to the strip. Filter 17 and collector 16 have complementary means 22, 23 to contact them and allows the fluid to flow through the filter material, then to the strip 18.

Case 19 is a generally cylindrical container made of a non-transparent material closed at its bottom end 24 and open at its opposed end 25 to enable loading with all of the above described components of the test device. Precise positioning of these components inside case 19 is ensured by complementary internal forms. This device requires a reading device having a complementary circular opening.

Figure 4:
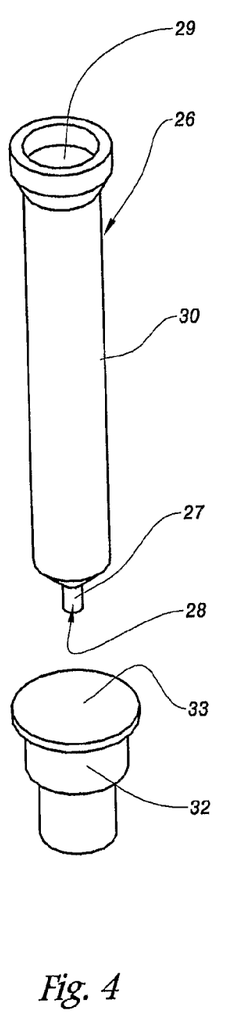
FIG. 4 is a schematic representation of a third test device embodiment.

FIG. 4 shows a case 26 made of a non-transparent material and provided with a capillary 27 having an open capillary end 28 and an open top 29 with a chamber 30 disposed between. Chamber 30 accommodates a test strip which is kept in place through internal means (not represented). The capillary 27 is brought into contact with a sample liquid by touching the liquid with the capillary open end 28. The liquid in the capillary is then diluted and flushed into the chamber 30 with a buffer contained in a buffer container 32 that is sealed with a foil 33 which is pierceable with the capillary 27. After diffusion of the sample the buffer container is removed to allow one to place the case into the magnetic reader. Before use, container 32 is arranged on the top open end of the case, in the open top 29.

EXAMPLE

Hepatitis B Antigen Detection

I. Materials & Equipments
0.5 ml tube
96 wells microplate
Test devices: two strips made of nitrocellulose
Magnetic material: magnetic particles Estapor® (Merck KGaA)
Magnetic reader: it is constructed according to EP 1 262 766. It comprises a measure cell inside which an assay device including a strip may be placed for the reading operation. A cylindrical coil delimitates the reading space and is able to generate in this space a magnetic excitation (A/m) made of the superposition of two monochromatic frequencies $f_1$ and $f_2$. This coil also serves as a measuring coil. There are means to position the strip reading zone in the cylindrical space delimited by the coil. The distance between the coil and the reading zone on the strip may reach 5 mm. The presence of the magnetic material in the reading zone provokes a deformation of the power spectral density of the magnetic induction. Thus the magnetic induction spectra contains spectrum lines to the combined frequencies of the excitation frequencies ($f_{line}=n_1f_1\pm n_2f_2$ where $n_1$ and $n_2$ are positive integers). The intensity of these lines is proportional to the volume of magnetic material in the volume of reading. The reader further comprises a filter and an amplitude demodulator, allowing to measure the intensity of one or several spectral lines (here $f_1\pm 2f_2$). A lock-in amplifier (digital and/or analogic) allows to precisely determine the volume of non linear magnetic material in the reading zone.

In the example, frequencies $f_1$ and $f_2$ were respectively 100 kHz and 100 Hz.

II. Reagents $1^{st}$ conjugate: magnetic particles linked to monoclonal antibody against HBsAg subtype Ay $2^{nd}$ conjugate: magnetic particles linked to monoclonal antibody against HBsAg subtype Ad Migration buffer $1^{st}$ antigen: HBsAg subtype Ay $2^{nd}$ antigen: HBsAg subtype Ad III. Protocol a. Preparation of the Migration Suspension In a 0.5 ml tube, the $1^{st}$ conjugate was diluted at 0.2% in migration buffer and mix was performed through sonication. 75 µl of the Ay antigen suspension was added in a wells. 5 µl of the diluted conjugate was added in the well and mixed.

Same procedure for the $2^{nd}$ conjugate and antigen Ad.

b. Migration

The strips were contacted each with one of the suspensions in the wells and migration performed during 20 minutes.

c. Magnetic Reading

Figure 5:
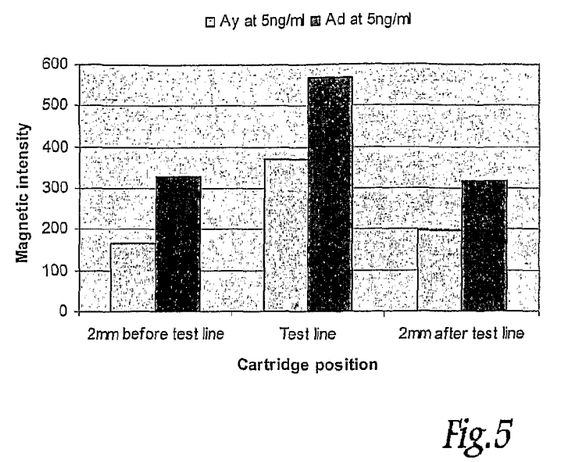
FIG. 5 is a graph representing the results of subtypes Ay and Ad Hepatitis B antigens analysis using two strips, the results being expressed in magnetic intensities measured at three points along the strip.

After migration, the testing devices were each introduced in the measure cell. The signal was analysed along the strip 2 mm before test line, on the test line and 2 mm after the test line. Results are presented on FIG. 5.

The invention claimed is:

1. A method for detecting and quantifying an analyte in a liquid sample, comprising:
    using a test strip and magnetic particles as a detectable label, wherein the magnetic particles exhibit a nonlinear magnetization characteristic,
        wherein said test strip has a sample-receiving zone, a reading zone and a movable entity bound to one or several magnetic particle(s), the test strip has a thickness (t) in the range of about 10 µm to about 10 mm and is made of a porous material that allows the liquid sample and the analyte to flow from the sample-receiving zone in the direction of and through the reading zone and wherein the test strip is arranged inside a case to form an assay device, the case surrounds the test strip and is provided with a sample window facing or in the vicinity of the sample-receiving zone to put the liquid sample into contact with the strip, wherein in its part surrounding the reading zone, the case is a continuous piece of a blind material that is permeable to an externally-generated magnetic field;
    positioning the assay device in a measure cell of a magnetic reading device which detects the amount of magnetic particles in the reading zone by submitting it to at least one excitation magnetic field having about 90% of its power within one frequency band or a plurality of frequency bands, wherein the reading device measures the induced magnetic response field outside said frequency band or said plurality of frequency bands; and
    detecting the analyte content of the sample, wherein detection of the amount of magnetic particles which become bound to the reading zone of the test strip is linked through a function to the analyte content of the sample.

2. The method according to claim 1, comprising a conjugate comprised of a reagent linked to the magnetic particles and wherein detection is based on a specific binding event between the analyte linked to the conjugate or the conjugate and a ligand immobilized in the reading zone of the test strip.

3. The method according to claim 1, wherein the assay device is placed in the measure cell in order to submit the reading zone to:
    a step of excitation of the magnetic particles located in the reading zone with an excitation magnetic field having a frequency component $f_1$ and a frequency component $f_2$, and
    a step of measuring the amplitude of the magnetic field induced by the magnetic particles in response to the excitation at a specific frequency component the f; frequency being related to frequency components $f_1$ and $f_2$ by the following relation:
        $f_i = n.f_1 \pm m.f_2$, where m and n are integers >0, at least one of m and n being different from 0 the frequency component $f_i$ amplitude being directly proportional to the amount of magnetic particles retained in the reading zone.

4. The method according to claim 3, wherein n is 1 and m is ±2.

5. The method according to claim 3, wherein n or m is zero.

6. The method according to claim 1, wherein the magnetic particles comprise a superparamagnetic material.

7. The method according to claim 6, wherein the superparamagnetic particles comprise a superparamagnetic material chosen among the group consisting of $Fe_2O_3$, $Fe_3O_4$ and mixtures thereof.

8. The method according to claim 1, wherein the measure cell comprises an excitation and/or measuring coil which delimitates a cylindrical reading space,
    wherein the assay device is placed in said space, and further wherein the magnetic excitation field is emitted in a plan transversal to the test strip so that the reading zone is entirely or substantially entirely submitted to the magnetic field.

9. The method according to claim 1, wherein a mixture of sample and magnetic particle containing labeled reagents is put on the sample receiving zone through the sample-introducing window.

10. The method according to claim 1, wherein the analyte is an antigen or an antibody.

11. The method according to claim 1, wherein the case is entirely made of a blind material.

12. An assay device for detecting and quantifying an analyte in a liquid sample comprising a test strip having a sample-receiving zone and a reading zone and a movable entity bound to one or several magnetic particle(s), the test strip being of such a material that allows the liquid sample and the analyte to flow from the sample-receiving zone in the direction of and through the reading zone, which test strip is arranged inside a case which surrounds the test strip and is provided with a sample window facing or in the vicinity of the sample-receiving zone to put the liquid sample into contact with the strip, wherein in its part covering the reading zone, the case is a continuous piece of a blind material that is permeable to an externally-generated magnetic field and wherein the test strip has a thickness (t) in the range of about 10 µm to about 10 mm.

13. The device of claim 12, wherein the strip thickness (t) is between about 0.1 mm and about 0.5 mm.

14. The device of claim 12, wherein the strip thickness (t) is above 0.5 mm and less or equal to about 2 mm.

15. The device of claim 12, wherein the test strip is made of a plurality of superimposed layers (plies).

16. The device of claim 12, wherein the test strip is made of a rolled sheet.

17. The device of claim 12, wherein the test strip has a three-dimensional reading zone containing an immobilized ligand which is specific for the analyte or an analogue thereof, said three-dimensional zone having the width ($Z_R$) between about 0.5 and about 5 mm.

18. The device of claim 17, wherein the three-dimensional reading zone has a width ($Z_R$) between about 2 and about 5 mm.

19. The device of claim 12, wherein the case is entirely made of a blind material.

20. The device of claim 12, wherein the device is positioned in a measure cell of a magnetic reading device that detects the amount of magnetic particles in the reading zone by measuring a magnetic field induced by the magnetic particles.

21. The device of claim 20, wherein the magnetic reading device comprises a coil that generates an excitation magnetic field to excite the magnetic particles in the reading zone and measures the magnetic field induced by the magnetic particles in response to the excitation magnetic field.

* * * * *